United States Patent [19]

Moon et al.

[11] 4,199,583

[45] Apr. 22, 1980

[54] ANTIFUNGAL METHOD, FORMULATIONS AND COMPOUNDS

[75] Inventors: Malcolm W. Moon; Diane M. Rohrstaff, both of Kalamazoo, Mich.

[73] Assignee: The Upjohn Company, Kalamazoo, Mich.

[21] Appl. No.: 749,982

[22] Filed: Dec. 13, 1976

Related U.S. Application Data

[63] Continuation of Ser. No. 607,096, Aug. 25, 1975, abandoned, which is a continuation of Ser. No. 54,562, Jul. 13, 1970, abandoned.

[51] Int. Cl.[2] .......... A01N 9/22

[52] U.S. Cl. .......... 424/251

[58] Field of Search .......... 424/251

[56] References Cited

U.S. PATENT DOCUMENTS 3,092,545 6/1963 Williamson .......... 424/251

3,219,522 11/1965 Gordon .......... 424/251

FOREIGN PATENT DOCUMENTS 3811148 5/1961 Japan .......... 424/251

OTHER PUBLICATIONS

*Chemical Abstracts,* vol. 49 4675e, (1955), vol. 55, 6491p, (1961).

*Primary Examiner*—Frederick E. Waddell
*Attorney, Agent, or Firm*—Martin B. Barancik

[57] ABSTRACT

Some known 4-amino-6-chloro-5-(H or $CH_3$)-2-(methylthio or methoxy)pyrimidines have been found to be active against fungi. The compounds are systemically active in plants, that is to say, the compounds are carried by plant juices to sites of infection. Other related compounds that are novel have the same activity and advantage. The compounds are prepared according to well-known methods. A new method and formulations for killing and controlling fungi are described.

40 Claims, No Drawings

ANTIFUNGAL METHOD, FORMULATIONS AND COMPOUNDS

CROSS REFERENCE TO RELATED APPLICATIONS

This is a continuation of pending application Ser. No. 607,096, filed Aug. 25, 1975, which is a continuation of application Ser. No. 54,562, filed July 13, 1970 both abandoned.

SUMMARY OF THE INVENTION

This invention pertains to a new method for killing and controlling fungi, new formulations for that purpose, and some new chemical compounds. The invention is more particularly directed to a method of killing and controlling fungi with 4-amino-6-halo-5-(H or $CH_3$)-2-(methylthio, methoxy, methylsulfinyl, or methylsulfonyl)pyrimidines, new formulations of the foregoing compounds with a dispersible solid carrier, and the new 2-(methylsulfinyl)- and 2-(methylsulfonyl)-pyrimidines.

Some of the active antifungal agents of this invention are known compounds, for example, 4-amino-6-chloro-2-(methylthio)pyrimidine has been tested for its effects on cell division, see Bull. Soc. Chem. Biol. 40, pp. 971–85 (1958). Moreover, the antiviral activity of 5-alkyl-4-amino-6-chloro-2-(methylthio)pyrimidines have (more than one compound was studied) been evaluated, see Chem. Pharm. Bull. 11, p. 495 (1963). These and other activity tests did not reveal to those skilled in the art that the compounds of this invention are antifungal agents (fungicides) systemically active in plants. The discovery of the heretofore unknown antifungal activity is the contribution of this invention.

Accordingly, an objective of this invention is to provide new antifungal agents. A further objective of this invention is to provide a new method for killing and controlling fungi wherever the organisms are found, including various objects of all types, including plants, and various situs. A still further objective of the invention is to provide new formulations for killing and controlling fungi, particularly dispersible formulations of the active components of this invention and a solid pulverulent carrier. These and other objectives of this invention will become apparent in the detailed description that follows.

The antifungal 4-amino-6-halo-5-(H or $CH_3$)-2-(methylthio, methoxy, methylsulfinyl, or methylsulfonyl)-pyrimidines of this invention have the structural formula in their free base form:

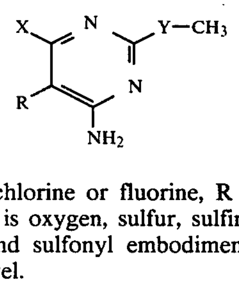

wherein X is chlorine or fluorine, R is hydrogen or methyl, and Y is oxygen, sulfur, sulfinyl, or sulfonyl. The sulfinyl and sulfonyl embodiments of the compounds are novel.

DETAILED DESCRIPTION OF THE INVENTION

The antifungal 4-amino-6-halo-5-(H or $CH_3$)-2-(methylthio, methoxy, methylsulfinyl, or methylsulfonyl)-pyrimidines of this invention are represented in Formula I, above, in the free base form. Those skilled in the art, however, will note that the amino group will associate with the hydrogen ions of a dissociated acid to form stable acid addition salts. The acid addition salts are contemplated as an embodiment of the invention. The acid addition salts are readily prepared, and are a convenient form of the compounds for antifungal purposes.

The compounds form monoacid addition salts, the hydrochlorides being representative, readily preparable, and preferred. The hydrochlorides are obtained by using hydrochloric acid or anhydrous hydrogen chloride. Other representative mineral acid addition salts are the hydrobromides, the hydroiodides, the sulfates, the phosphates, the hexafluorophosphates, the nitrates, the arsenates, and the fluosilicates.

The 4-amino-6-halo-5-(H or $CH_3$)-2-(methylthio, methoxy, methylsulfinyl, or methylsulfonyl)pyrimidines of Formula I and acid addition salts are active against fungi. Hence, the compounds can be used in the novel formulations of this invention to kill and control fungi on organic matter such as wood, cellulosic fibers, leather, seeds, fruits, and vegetables, living plants; soil; and on animals such as fish, reptiles, birds, cattle, horses, dogs, cats, and other animals. The invention provides, therefore, a new means of killing and controlling fungi in general as well as specific fungi that are pathogenic to seeds, plants, and animals. In particular, compounds of this invention have been found to be effective against *Verticillium dahliae, Rhizoctonia solani,* and *Pythium ultimum* by in vitro tests. In bean plant tests, systemic activity against bean rust (*Uromyces phaseoli*), and wheat rust (*Puccinia graminis* var. tritici), and *Sclerotium rolfsii* was observed. Illustratively, an effective compound against the foregoing fungi is 4-amino-6-chloro-2-(methylthio)pyrimidine. The compound was also active in agar dilution tests against *Currularia spicifica, Fusarium solani, Helminthosporium victorise,* Rhizoctonia, and *Sclerotium rolfisii.* It is particularly effective against Basidiomycetes.

Other fungi against which the compounds of this invention are prospectively active include: *Botrytis cinerea, Fusarium oxysporum, Monolinia fructicola, Pythium debaryanum,* Stemphyllium species, *Blastomyces dermatitidis, Coccidioides immitis, Histoplasma capsulatum, Trychophyton rubrum, Trichophyton violaceum,* and *Trichophyton metagrophytes.*

The antifungal 4-amino-6-halo-5-(H or $CH_3$)-2-(methylthio, methoxy, methylsulfinyl, or methylsulfonyl)-pyrimidines are prepared using conventional procedures. Two methods for preparing the known compound 4-amino-6-chloro-2-(methylthio)pyrimidine are described in the chemical literature.

According to a method described by Baker, Joseph, and Schaub, J. Org. Chem. 19, p. 631 (1954) ethyl cyanoacetate is reacted with thiourea in the presence of sodium methoxide to give 4-amino-6-hydroxy-2-mercaptopyrimidine which is methylated in situ to obtain 4-amino-6-hydroxy-2-(methylthio)pyrimidine. Chlorination of the latter compound with phosphorus oxychloride in dimethylaniline gives the desired 4-amino-6-chloro-2-(methylthio)pyrimidine. Yields using this method are uncertain.

Another method described by Wheeler and Jamieson, Am. Chem. J. 32, p. 345 (1904) initiates the synthesis with 2-thiobarbituric acid which is methylated. Either dimethylsulfate or methyl iodide is used to obtain 4,6- dihydroxy-2-methylthiopyrimidine. Dichlorination at 4- and 6- positions is accomplished with phosphorus oxychloride in the presence of dimethylaniline, and the 4,6-dichloro-2-(methylthio)pyrimidine thus obtained is reacted with aqueous alcoholic ammonia to produce the desired 4-amino-6-chloro-2-(methylthio)pyrimidine.

The dichlorination step, above, is followed by removal of excess phosphorus oxychloride by evaporation. The residual oil thus obtained is advisedly treated with a mixture of crushed ice and concentrated ammonia in order to destroy any remaining phosphorus oxychloride. This treatment facilitates final removal of the dimethylaniline from the 4,6-dichloro-2-(methylthio)-pyrimidine.

The final step of amination with ammonia requires heating at 100° C. Too high temperatures (around 170° C.) will result in replacement of both chlorine atoms instead of only at the 4-position. The length of heating can range from about 4 to 20 hours, preferably 6 to 16 hours. An autoclave is used for heating in order to avoid loss of the alcoholic medium, preferably ethanol.

After heating and amination is completed, the reaction mixture can be diluted with water to effect separation of the product. Alternatively, the reaction mixture can be concentrated by removing some of the water and alcohol by evaporation.

Purification of the desired product is finally accomplished by crystallization. Numerous solvents and mixtures of solvents can be used, advantageously, diethyl ether and petroleum ether (preferred), methanol, and ethyl acetate.

The new 4-amino-6-halo-2-(methylsulfinyl and methylsulfonyl)pyrimidines of this invention are prepared by conventional oxidation of 4-amino-6-halo-2-(methylthio)pyrimidine. Advantageously, oxidation is accomplished using hydrogen peroxide and an alkanoic acid medium, e.g., acetic (preferred), propionic, or formic acid. Alternatively, oxidation to the sulfone can be accomplished by reaction of the sulfur atom with gaseous chlorine in the presence of water or an alcohol.

EXAMPLE 1—Preparation of 4-Amino-6-chloro-2-(methylthio)pyrimidine

Part A—2-(Methylthio)-4,6-pyrimidinediol

A quantity (72.07 g., 0.5 mole) of 2-thiobarbituric acid was dissolved in a reaction medium consisting of 500 ml. methanol, 500 ml. water, and 20 g. sodium hydroxide. The medium was heated in order to effect solution. After cooling the solution to 41° C., 142 g. (1.0 mole) methyl iodide was added, with stirring. The reaction mixture was heated at the reflux temperature for 1 hr. The desired 2-(methylthio)-4,6-pyrimidinediol crystallized out as the refluxing continued, and it was recovered on a filter by cooling the reaction mixture to 60° C. and filtering. The initial crop of crystalline product weighed 51.5 g. and had a melting point at >300° C. After refrigerating the mother liquor, an additional 19.08 g. of product was obtained.

Part B—4,6-Dichloro-2-(methylthio)pyrimidine

A reaction mixture consisting of 46.6 g. (0.28 mole) 2-(methylthio)-4,6-pyrimidinediol (prepared in Part A above), 465 ml. phosphorus oxychloride, and 35.7 g. (0.28 mole) N,N-dimethylaniline was heated at the reflux temperature for 6 hrs. The excess and unreacted phosphorus oxychloride was removed by evaporation under reduced pressure, and the oily residue that remained was dissolved in 500 ml. chloroform. The N,N-dimethylaniline activator was removed from the chloroform solution by forming the hydrochloride acid addition salt which is soluble in water and is removed by extraction with water. This procedure was preliminarily accomplished by treating the chloroform solution with three, 100 ml. portions of 10% aqueous hydrochloric acid. Two final extractions with 100 ml. portions of water gave a tertiary amine free chloroform solution that was dried over anhydrous sodium sulfate. The chloroform was then removed by evaporation under reduced pressure to give 38.1 g. of solid. The solid was recrystallized from petroleum ether to give 32.3 g. of 4,6-dichloro-2-(methylthio)pyrimidine having a melting point at 44° to 45.5° C.

Part C—4-Amino-6-chloro-2-(methylthio)pyrimidine

A reaction mixture consisting of 124.7 g. (0.64 mole) 4,6-dichloro-2-(methylthio)pyrimidine (prepared as in Part B, above), 500 ml. ethanol, and 250 ml. of substantially saturated aqueous ammonia was heated, with stirring, at 100° C. in an autoclave for 6 hrs. After cooling the reaction mixture, water was added, and a precipitate formed. The precipitate was collected on a filter, and recrystallized from a mixture of ether and petroleum ether to give 40 g. of the desired 4-amino-6-chloro-2-(methylthio)pyrimidine having a melting point at 130° to 131° C.

EXAMPLE 2—Preparation of 4-Amino-6-chloro-2-(methylsulfinyl)pyrimidine

A reaction mixture consisting of 6.0 g. 4-amino-6-chloro-2-(methylthio)pyrimidine (prepared in Example 1, Part C, above) dissolved in 48 ml. acetic acid with 7.2 ml. 30% hydrogen peroxide (by wt.) was set aside with stirring for 1 hr. After removing some of the volatile components by evaporation under reduced pressure, a solid separated. The solid was collected on a filter and the filter cake was washed with methanol. There was thus obtained 5.5 g. of 4-amino-6-chloro-2-(methylsulfinyl)pyrimidine having a melting point at 245° C. (with decomposition). Recrystallization from 500 ml. ethyl alcohol gave two crops of crystals. One crop had a melting point at 252° to 257° C. (and the other had a melting point at 255° to 260° C.) (Both with decomposition).

Analysis: Calc'd. for $C_5H_6ClN_3OS$: C, 31.33; H, 3.16; Cl, 18.50; N, 21.93;S, 16.92 Found: C, 31.63; H, 3.40; Cl, 18.75; N, 22.09;S, 16.82

EXAMPLE 3

Following the same procedure as Example 1, Parts A, B, and C, but substituting 5-methyl-2-thiobarbituric acid, for 2-thiobarbituric acid, there is prepared the corresponding
5-methyl-2-(methylthio)-4,6-pyrimidinediol,
4,6-dichloro-5-methyl-2-(methylthio)pyrimidine, and
4-amino-6-chloro-5-methyl-2-(methylthio)pyrimidine,
respectively.

EXAMPLE 4—Preparation of 4-Amino-6-chloro-2-methoxypyrimidine

4-Amino-2,6-dichloropyrimidine (0.5 g.) was added to 30 ml. of a 1% solution of sodium methoxide in methanol. The resultant solution was heated at the reflux temperature for 2 hrs. The methanol was then removed by evaporaion and water was added to the residual oil. The precipitate that formed was filtered off, washed with water and dried at 100° C. at a pressure of 100 mm for 18 hrs. There was thus obtained 4-amino-6-chloro-2-methoxypyrimidine having a melting point at 124° C.

EXAMPLE 5

Following the procedure of Example 2, but substituting 4-amino-6-chloro-5-methyl-2-(methylthio)pyrimidine, for 4-amino-6-chloro-2-(methylthio)pyrimidine, there is prepared 4-amino-6-chloro-5-methyl-2-(methylsulfinyl)pyrimidine.

EXAMPLE 6

Reacting 4-amino-6-chloro-2-(methylthio)pyrimidine and 4-amino-6-chloro-5-methyl-2-(methylthio)pyrimidine, respectively, with hydrogen peroxide in the presence of acetic acid at about 50° C. and removing the excess hydrogen peroxide and acetic acid by evaporation, under reduced pressure, there is obtained the corresponding 4-amino-6-chloro-2-(methylsulfonyl)pyrimidine and
4-amino-6-chloro-5-methyl-2-(methylsulfonyl)pyrimidine,
respectively.

EXAMPLE 7—Preparation of 4-amino-6-chloro-2-(methylthio)pyrimidine hydrochloride To a solution of 4-amino-6-chloro-2-methylthiopyrimidine (9.5 g.) in 95% aqueous ethanol (20 ml.) at 50° C. was added 20 ml. of a saturated solution of hydrogen chloride in ethanol. The solution was chilled to 0° C. and the precipitate was filtered off, washed with cold ethanol and dried at 50° C. under reduced pressure. There was thus obtained 8.6 g. of 4-amino-6-chloro-2-(methylthio)pyrimidine hydrochloride having a melting point at 203° C. (with decomposition).

Following the same procedure, but substituting 4-amino-6-chloro-5-methyl-2-(methylthio)pyrimidine, 4-amino-6-chloro-2-(methoxy)pyrimidine, 4-amino-6-chloro-5-methyl-2-(methylsulfinyl)pyrimidine and 4-amino-6-chloro-2-(methylsulfonyl)pyrimidine for 4-amino-6-chloro-2(-methyl-thio)-pyrimidine hydrochloride there were prepared the corresponding 4-amino-6-chloro-5-methyl-2-(methylthio)pyrimidine hydrochloride, 4-amino-6-chloro-2-(methoxy)pyrimidine hydrochloride, 4-amino-6-chloro-5-methyl-2-(methylsulfinyl)pyrimidine hydrochloride, and 4-amino-6-chloro-2-(methylsulfonyl)pyrimidine, respectively.

The 4-amino-6-halo-5-(H or $CH_3$)-2-(methylthio, methoxy, methylsulfinyl, or methylsulfonyl)pyrimidines (free base compounds of Formula I and acid addition salts thereof) are formulated as antifungal agents with solid and liquid carries with or without adjuvants. The compounds can be used in pure form, but generally the interest of economy is best served by the formulations of the invention. The pure active compounds (including mixtures thereof) or the formulations can be applied to fungi, objects, or a situs for preventing fungal growth and propagation. The antifungal formulations of this invention include dispersions in powder and granular carriers, e.g., dusts and granules, dispersions in liquid carriers, e.g., true solutions, suspensions and emulsifiable concentrates; smokes and aerosols; emulsions, e.g., creams and ointments; and capsules and tablets.

The 4-amino-6-halo-5-(H or $CH_3$)-2-(methylthio, methoxy, methylsulfinyl, or methylsulfonyl)pyrimidines can be readily formulated as dusts by grinding a mixture of the compound and a pulverulent carrier in the presence of each other. Grinding is conveniently accomplished in a ball mill, a hammer mill, or by air-blast micronization. A suitable ultimate particle size is less than 60 microns. Preferably, 95% of the particles are less than 50 microns, and about 75% are 5 to 20 microns. Dusts of that degree of comminution are conveniently free-flowing and can be applied to animals, inanimate matter, fruit trees, crop plants, and soil so as to effect thorough distribution and coverage. Dusts are particularly adapted for effectively controlling plant fungi over wide areas when applied by airplane. They are also indicated for application to the undersides of plant foliage and the skin of hairy animals.

Representative suitable pulverulent carriers include the natural clays such as China, Georgia, Barden, attapulgus, kaolin, and bentonite clays; minerals in their natural forms as they are obtained from the earth such as talc, pyrophyllite, quartz, diatomaceous earth, fuller's earth, chalk, rock phosphates and sulfates, calcium carbonates, sulfur, silica and silicates; chemically modified minerals such as washed bentonite, precipitated calcium phosphate, precipitated calcium carbonate, precipitated calcium silicate, synthetic magnesium silicate, and colloidal silica; and organic flours such as wood walnut shell, soybean, cottonseed, and tobacco flours, and free-flowing, hydrophobic starches.

Dusts can also be prepared by dissolving the 4-amino-6-halo-5-(H or $CH_3$)-2-(methylthio, methoxy, methylsulfinyl, or methylsulfonyl)pyrimidines in a volatile solvent such as methylene chloride, mixing the solution with a pulverulent carrier and evaporating the solvent.

The proportions of pulverulent carrier and 4-amino-6-halo-5-(H or $CH_3$)-2-(methylthio, methoxy, methylsulfinyl, or methylsulfonyl)pyrimidines can vary over a wide range depending upon the fungi to be killed or controlled and the conditions of treatment. In general, dust formulations can contain up to about 90% (on a weight basis) of the active ingredient. Dusts having as little as 0.001% of the active ingredient can be used, but a generally preferred proportion is from about 0.50% to about 20% of active ingredient.

The dispersible powder formulations of this invention are prepared by incorporating a surfactant in a dust composition prepared as described above. When about 0.1% to about 12% of a surfactant is incorporated in a dust, the dispersible powder thus obtained is particularly adapted for further admixture with water for spraying on inanimate matter and products, fruit trees, field crops, soil, and livestock. The dispersible powders can be admixed with water to obtain any desired concentration of active ingredient, and the mixture can be applied in amounts sufficient to obtain predetermined rates of application and uniform distribution. With this flexibility in mind, the dispersible powders of the invention can conveniently comprise preferably about 10% to about 80% of active ingredient.

Representative surfactants useful for preparing dispersible powder formulations of this invention include alkyl sulfates and sulfonates, alkyl aryl sulfonates, sulfosuccinate esters, polyoxyethylene sulfates, polyoxyethylene-sorbitan monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. The preferred class of surfactants includes blends of sulfonated oils and polyalcohol carboxylic acid esters (Emcol H-77), blends of polyoxyethylene ethers and oil-soluble sulfonates (Emcol H-400), blends of alkyl aryl sulfonates and alkylphenoxy polyethoxy ethanols (Tritons X-151, X-161, and X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul $N_4S$). It will be understood, of course, that the sulfate and sulfonate surfactants suggested above will preferably be used in the form of their soluble salts, for example, their sodium salts. All of these surfactants are capable of reducing the surface tension of water to less than about 40 dynes per centimeter in concentrations of about 1% or less. The dispersible powder compositions can be formulated with a mixture of surfactants of the types indicated if desired.

A suitable dispersible powder formulation is obtained by blending and milling 327 lb.s of Georgia Clay, 4.5 lbs. of isooctylphenoxy polyethoxy ethanol (Triton X-100) as a wetting agent, 9 lbs. of a polymerized sodium salt of substituted benzoid long-chain sulfonic acid (Daxad 27) as a dispersing agent, and 113 lbs. of the active ingredient. The resulting formulation has the following percentage composition (parts herein are by weight unless otherwise specified):

Active ingredient—25%

Isooctylphenoxy polyethoxy ethanol—1%

Polymerized sodium salt of substituted benzoid long-chain sulfonic acid—2%

Georgia Clay—72%

This formulation, when dispersed in water at the rate of 10 lbs. per 100 gals., gives a spray formulation containing about 0.3% (3000 ppm) active ingredient which can be applied to fungus infected soil, plants, or turf at the rate of 40 gals. per acre to give a total application of active ingredient of 1 lb. per acre.

If desired, dispersants such as methyl cellulose, polyvinyl alcohol, sodium ligninsulfonates, and the like can be included in the dispersible powder formulations of this invention. Adhesive or sticking agents such as vegetable oils, naturally occurring gums, casein, and others can also be included. Corrosion inhibitors such as epichlorohydrin and antifoaming agents such as stearic acid can also be included.

The granular formulations according to this invention are prepared by permeating a granular carrier with a solution of a 4-amino-6-halo-5-(H or $CH_3$)-2-(methylthio, methoxy, methylsulfinyl, or methylsulfonyl)-pyrimidines and then drying the granules. Suitable granular carriers include vermiculite, expanded vermiculite, pyrophyllite, and attapulgite. Suitable solvents include acetone, methylethyl ketone, and methylene chloride. A solution of, for example, 4-amino-6-chloro-2-(methylthio)pyrimidine is sprayed on a granular carrier while the carrier is being mixed and tumbled. The granules are then dried. The granules can range in size from about 10 to about 60 mesh, preferably about 30 to 60 mesh.

The compounds of this invention can be applied to fungi, objects, or a situs in aqueous sprays without a solid carrier. Since, however, many of the compounds themselves (particularly the free bases) are relatively insoluble in water, such compounds are preferably dissolved in a suitable inert organic solvent carrier. Advantageously, the solvent carrier is immiscible with water so that an emulsion of the solvent carrier in water can be prepared. If, for example, a water-miscible solvent carrier such as ethanol is used the solvent carrier will dissolve in the water and any excess 4-amino-6-halo-5-(H or $CH_3$)-2-(methylthio, methoxy, methylsulfinyl, or methylsulfonyl)pyrimidines will be thrown out of solution. In an oil-in-water emulsion, the solvent phase is dispersed in the water phase and the dispersed phase contains the active ingredient. In this way, uniform distribution of a water insoluble active ingredient is achieved in an aqueous spray. A solvent carrier in which the compounds are highly soluble is desirable so that relatively high concentrations of active ingredient can be obtained. Sometimes, one or more solvent carriers with or without a cosolvent can be used in order to obtain concentrated solutions of the active ingredient, the main consideration being to employ a water-immiscible solvent for the active ingredient that will hold the compound in solution over the range of concentrations useful for preventing fungal growth and propagation.

The emulsifiable concentrates of the invention are prepared, therefore, by dissolving the active ingredient and a surfactant in a substantially water-immiscible solvent carrier (i.e., a solvent carrier which is soluble in water to the extent of less than 2.5% by volume at temperatures of the order of 20° to 30° C.), for example, cyclohexanone, methyl propyl ketone, summer oils, ethylene dichloride, aromatic hydrocarbons such as benzene, toluene, and xylene, and high-boiling petroleum hydrocarbons such as kerosene, diesel oil, and the like. If desired, a cosolvent such as methyl ethyl ketone, acetone, isopropanol, and the like can be included with the solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed, if desired.

Advantageously, the concentration of active ingredient in the emulsifiable concentrates can range from about 5% to about 50% by weight, preferably from about 10% to about 40%. A concentrate comprising 20% (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Similarly, 1 qt. of a 20% concentrate mixed with 40 gals. of water provides about 1200 ppm (parts per million) of active ingredient. In the same manner, more concentrated solutions of active ingredient can be prepared.

The concentrate formulations of the invention which are intended for use in the form of aqueous dispersions or emulsions can also comprise a humectant, that is to say, an agent which will delay the drying of the composition in contact with material to which it has been applied. Suitable humectants include glycerol, diethylene glycol, solubilized lignins, such as calcium ligninsulfonate, and the like.

The rates of application to fungi, objects or situs will depend upon the species of fungi to be controlled, the presence or absence of desirable living organisms, temperature conditions of treatment, and the method and efficiency of application. In general, fungicidal activity is obtained when the compounds are applied at concentrations of about 10 to about 6000 ppm, preferably at concentrations of about 100 to about 1200 ppm.

The compositions containing 4-amino-6-halo-5-(H or $CH_3$)-2-(methylthio, methoxy, methylsulfinyl, or methylsulfonyl)pyrimidines according to the invention, can be applied by conventional methods to fungi, objects or any situs where control of fungi is desired. For example, an area of soil or plants can be treated by spraying wettable powder suspensions, emulsions, or solutions from boom-type powder sprayers or from hand-operated knapsack sprayers. Dusts can be applied by power-dusters, or by hand-operated dusters. Creams and ointment formulations can be applied to skin or objects for prolonged protection against the microorganisms.

EXAMPLE 8

A dispersible powder concentrate having the following percentage composition:

4-amino-6-chloro-2-(methylthio)pyrimidine—45.8%
Polymerized sodium salt of substituted benzoid long-chain sulfonic acid (Daxad 27)—9.2%
Kaolinite—45.0% was prepared by mixing 250 gm. 4-amino-6-chloro-2-(methylthio)pyrimidine, 50 gm. of a polymerized sodium salt of substituted benzoid long-chain sulfonic acid (Daxad 27), and 245 gm. of kaolinite. The mixture was milled to a particle size averaging 5 to 30 microns. It was suspended in 10 gals. of water, giving an aqueous spray containing about 6500 parts per million of active ingredient.

EXAMPLE 9

A fine granular formulation having the following percentage composition:

4-amino-6-chloro-5-methyl-2-(methylthio)-pyrimidine—3.7%
Expanded vermiculite (30/60 mesh)—96.3% was prepared by spraying a solution of 220 gm. of 4-amino-6-chloro-5-methyl-2-(methylthio)pyrimidine in 1000 ml. of methylene chloride on 5780 gm. of expanded vermiculite (30 to 60 mesh) while the vermiculite was being tumbled and stirred so as to assure even distribution. The methylene chloride was then evaporated, leaving 4-amino-6-chloro-5-methyl-2-(methylthio)pyrimidine adsorbed on the vermiculite particles, and the vermiculite was pulverized.

EXAMPLE 10

An emulsifiable concentrate having the following percentage composition:

4-amino-6-chloro-2-(methylsulfinyl)-pyrimidine—15.0%
Technical alkyl naphthalene boiling at 238° to 293° C. (Velsicol AR50)—19.7%
Xylene—17.4%
Isopropanol—17.4%
Ethylene dichloride—25.4%
Blend of alkyl aryl sulfonates and alkylphenoxy polyethoxy ethanols (Triton X-151)—5.1% was prepared by mixing 15.0 lbs. of 4-amino-6-chloro-2-(methyl-sulfinyl)pyrimidine, 19.7 lbs. of Velsicol AR 50, 17.4 lbs. of xylene, 17.4 lbs. of isopropanol, 25.4 lbs. of ethylene dichloride, and 5.1 lbs. of Triton X-151.

6.67 lbs. of the concentrate mixed with 10 gal. of water gave a spray emulsion containing 11,000 ppm of 4-amino-6-chloro-2-(methylsulfinyl)pyrimidine.

EXAMPLE 11

An emulsifiable concentrate having the following percentage composition:

4-amino-6-chloro-2-(methylthio)pyrimidine hydrochloride—40.0%
Technical alkyl naphthalene boiling at 238° to 293° C. (Velsicol AR50)—13.7%
Xylene—12.3%
Isopropanol—11.3%
Ethylene dichloride—17.7%
Blend of alkyl aryl sulfonates and alkylphenoxy polyethoxy ethanols (Triton X-151)—5.0% was prepared by mixing 40.0 lbs. of 4-amino-6-chloro-2-(methylthio)pyrimidine hydrochloride, 13.7 lbs. of Velsicol AR50, 12.3 lbs. of xylene, 11.3 lbs. of isopropanol, 17.7 lbs. of ethylene dichloride, and 5.0 lbs. of Triton X-151.

1.67 lbs. of the concentrate mixed with 10 gals. of water gave a spray emulsion containing 8,000 ppm of 4-amino-6-chloro-2-(methylthio)pyrimidine hydrochloride.

EXAMPLE 12

A wettable powder concentrate having the following percentage composition:

4-amino-6-chloro-2-(methoxy)pyrimidine—50%
Kaolinite clay (finely divided)—46%
Sodium salt of condensed mononaphthalene sulfonic acid (Lomar D)—4% was prepared by mixing 50 g. of 4-amino-6-chloro-2-methoxypyrimidine, 46 g. of the kaolinite clay, and 4 g. of Lomar D. The mixture was milled to an average particle size of 5 to 30 microns.

EXAMPLE 13

A granular formulation having the following percentage composition:

4-amino-6-chloro-2-(methylthio)pyrimidine—1%
Pyrophyllite (30/60 mesh)—99% was prepared by dissolving 1.0 lb. of 4-amino-6-chloro-2-(methylthio)pyrimidine in 10.0 l. of ethylene dichloride and spraying the solution on 99.0 lbs. of pyrophyllite. The granules were dried and then packaged for use.

EXAMPLE 14

An evaluation of the systemic efficacy of 4-amino-6-chloro-2-(methylthio)pyrimidine against bean rust was made by applying the compound to the soil of potted healthy bean plants, later inoculating the plants with bean rust spores, and subsequently comparing the amount of infection on treated plants with similarly inoculated but untreated (control) bean plants.

In this test, Pinto bean plants at the trifoliate stage of growth in 3" pots, were treated with 10 mg., 5 mg., and 2.5 mg. per pot of 4-amino-6-chloro-2-(methylthio)-pyrimidine. The plants were inoculated with bean rust spores 3, 8, and 14 days after treatment. Infection was established by spraying an aqueous inoculum on the foliage and keeping the plants in a high humidity chamber (about 100%) at about 70° F. for 10–15 hrs. Readings were made 6 to 7 days after the inoculation when spore formation on the bean leaves was evident enough for visual comparative evaluation. Results were as follows (in terms of percentage control as compared with inoculated but untreated plants).

| | Days (Post-drench) | | |
|---|---|---|---|
| Rate | 3 | 8 | 14 |
| 10 mg. | 100% | 100% | 100% |
| 5 mg. | 50% | 100% | 100% |
| 2.5 mg. | 15% | 75% | 10% |

These data show that 4-amino-6-chloro-2-(methylthio)pyrimidine is rapidly absorbed and translocated by growing bean plants, and that bean rust is controlled. After 14 days, the 2.5 mg. rate was losing efficacy rapidly but at 8 days control was 75% better than untreated plants.

Similar efficacy is obtained with the other compounds of this invention, including the new 4-amino-6-chloro-2-(methylsulfinyl)pyrimidine.

We claim:

1. The method of killing and controlling fungi which comprises applying to fungi, objects, or a situs, an antifungal amount of a compound of the formula:

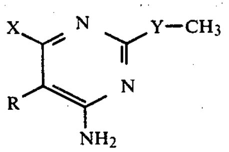

wherein X is chlorine or fluorine, Y is sulfinyl, and R is hydrogen or methyl; or an acid addition salt thereof.

2. The method of claim 1 wherein a free base compound is applied.

3. The method of claim 2 wherein the compound is 4-amino-6-chloro-2-(methylsulfinyl)pyrimidine.

4. The method of claim 1 wherein a compound is applied in combination with a dispersible carrier.

5. The method of claim 4 wherein the combination includes a surfactant.

6. An antifungal formulation comprising a dispersible solid carrier and as essential active component an antifungal effective amount of a compound having the formula:

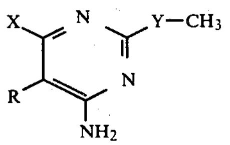

wherein X is chlorine or fluorine, Y is sulfinyl, and R is hydrogen or methyl; or an acid addition salt thereof.

7. A formulation of claim 6 wherein a surfactant is present.

8. A formulation of claim 7 wherein the active component is a free base.

9. A formulation of claim 8 wherein the active component is 4-amino-6-chloro-2-(methylsulfinyl)pyrmidine.

10. Vermiculite impregnated with an antifungal effective amount of a compound of the formula:

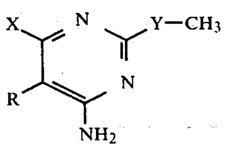

wherein X is chlorine or fluorine, Y is sulfinyl and R is hydrogen or methyl; acid addition salt thereof.

11. The combination of claim 10, wherein a free base compound is applied.

12. The combination according to claim 11, wherein the compound is 4-amino-6-chloro-2-(methylsulfinyl)-pyrimidine.

13. A metod of killing or controlling fungi which comprises applying to fungi, objects, or a situs an antifungal effective amount of a compound of the formula

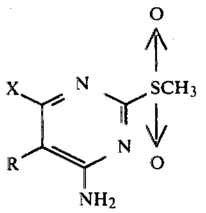

wherein X is chlorine or fluorine and R is hydrogen or methyl; or an acid addition salt thereof.

14. The method of claim 13 wherein a free base compound is applied.

15. The method of claim 14 wherein X is chloro and R is hydrogen.

16. The method of claim 13 wherein the compounds are applied in combination with a dispersible carrier.

17. The method of claim 16 wherein the combination includes a surfactant.

18. An anti-fungal formulation comprising a dispersible solid carrier and as essential active component, an antifungal effective amount of a compound of the formula

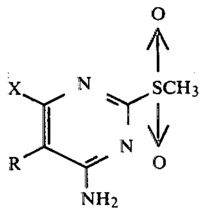

wherein X is chlorine or fluorine and R is hydrogen or methyl; or an acid addition salt thereof.

19. A formulation of claim 18 wherein a surfactant is present.

20. A formulation of claim 18 wherein the active compound is a free base.

21. A formulation of claim 20 wherein X is chloro and Y is hydrogen.

22. Vermiculite impregnated with an anti-fungal effective amount of a compound of the formula

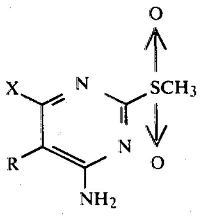

wherein X is chlorine or fluorine and R is hydrogen or methyl; or an acid addition salt thereof.

23. The vermiculite of claim 22 wherein a free base compound is employed.

24. The vermiculite of claim 23 wherein X is chlorine and R is hydrogen.

25. The method of killing or controlling fungi *Uromyces phaseoli which comprises administering to said fungi, object or situs, an anti-Uromyces phaseoli* systemically effective amount of a compound of the formula

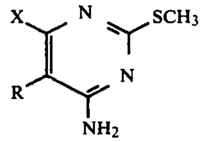

wherein X is chlorine or fluorine and R is hydrogen methyl; or an acid addition salt thereof.

26. The method of claim 25 wherein the free base is administered.

27. The method of claim 26 wherein X is chlorine and R is hydrogen.

28. The method of claim 26 wherein X is chlorine and R is methyl.

29. The method according to claim 25 wherein the compound is applied in combination with a dispersible carrier.

30. The method according to claim 29 wherein the combination includes a surfactant.

31. An anti-fungal formulation comprising a dispersible solid carrier and as essential active component an anti-*Uromyces phaseoli* or *Puccinia graminis* var. tratici systemically effective amount of a compound selected from free bases of the formula

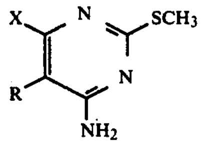

wherein X is chlorine or fluorine and R is hydrogen or methyl; or an acid addition salt thereof.

32. A formulation of claim 31 wherein a surfactant is present.

33. A formulation of claim 32 wherein the active component is a free base.

34. A formulation of claim 33 wherein X is chlorine and R is hydrogen.

35. A formulation of claim 33 wherein X is chlorine and R is methyl.

36. Vermiculite impregnated with an anti-*Uromyces phaseoli* or *Puccinia graminis* var. tritici systemically effective amount of a compound of the formula

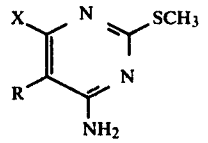

wherein X is chlorine or fluorine and R is hydrogen or methyl; or an acid addition salt thereof.

37. The vermiculite of claim 36 wherein the free base is present.

38. A vermiculite of claim 37 wherein X is chlorine and R is hydrogen.

39. A vermiculite of claim 38 wherein X is chlorine and R is methyl.

40. A vermiculite of claim 38 wherein the vermiculite is expanded.

* * * * *